United States Patent
Zhao et al.

(10) Patent No.: US 11,542,482 B2
(45) Date of Patent: Jan. 3, 2023

(54) **RICE SERINE HYDROXYMETHYLTRANSFERASE CODED GENE *OSSHM4* MUTANTS AND APPLICATION THEREOF**

(71) Applicant: Nanjing Agricultural University, Jiangsu (CN)

(72) Inventors: Fangjie Zhao, Jiangsu (CN); Jie Chen, Jiangsu (CN); Zhong Tang, Jiangsu (CN); Xinyuan Huang, Jiangsu (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 0 days.

(21) Appl. No.: 16/774,291

(22) Filed: Jan. 28, 2020

(65) Prior Publication Data

US 2021/0261927 A1    Aug. 26, 2021

(51) Int. Cl.
  *C12N 9/10*      (2006.01)
  *C12N 15/82*     (2006.01)

(52) U.S. Cl.
  CPC ....... *C12N 9/1014* (2013.01); *C12N 15/8261* (2013.01); *C12Y 201/02001* (2013.01)

(58) Field of Classification Search
  None
  See application file for complete search history.

(56) References Cited

PUBLICATIONS

Matsusaka et al. "Serine hydroxymethyltransferase participates in the synthesis of cysteine-rich storage proteins in rice seed". Plant Science. 312(111049): 1-8. (Year: 2021).*

Chen et al. "Mutation in OsCADT1 enhances cadmium tolerance and enriches selenium in rice grain". New Phytologist. 226:838-850. (Year: 2020).*

N.J. Barrow and B.R. Whelan, "Testing a mechanistic model. VIII. The effects of time and temperature of incubation on the sorption and subsequent desorption of selenite and selenate by a soil", Journal of Soil Science, 1989, vol. 40, pp. 29-37.

Chen L. et al., "Determination of Selenium Concentration of Rice in China and Effect of Fertilization of Selenite and Selenate on Selenium Content of Rice", Journal Agricultural and Food Chemistry, 2002, vol. 50, pp. 5128-5130.

Combs Jr., G. F., "Selenium in global food systems", British Journal of Nutrition, 2001, vol. 85, pp. 517-547.

(Continued)

*Primary Examiner* — Matthew R Keogh
*Assistant Examiner* — David R Byrnes
(74) *Attorney, Agent, or Firm* — Gary J. Gershik

(57) ABSTRACT

The present invention discloses rice serine hydroxymethyltransferase coded gene OsSHM4 mutants and application thereof. The rice serine hydroxymethyltransferase coded gene mutants are obtained in a manner that T at a 461st position of a CDS sequence region of a wild type rice OsSHM4 gene is mutated to C, so that coded amino acids thereof are mutated from leucine to proline. A CDS sequence of the wild type rice OsSHM4 gene is shown in SEQ ID NO. 1. After mutation of serine hydroxymethyltransferase coded genes OsSHM4, under a field experiment condition, S and Se content of rice shoots is remarkably improved without influencing biomass of rice. After wild type serine hydroxymethyltransferase coded genes OsSHM4 are genetically modified to complement the mutants, S and Se content of shoots of complemented strains is restored to that of wild type rice water planting.

14 Claims, 3 Drawing Sheets

Specification includes a Sequence Listing.

(56) References Cited

PUBLICATIONS

El-Ramady, H. et al., "Selenium in soils under climate change, implication for human health", Environ Chem Lett, 2014, DOI:10.1007/s10311-014-0480-4, pp. 1-19.

Hawkesford, M. J. and Zhao, F., "Strategies for increasing the selenium content of wheat", Journal of Cereal Science, 2007, vol. 46, pp. 282-292.

Sors, T.G. et al., "Selenium uptake, translocation, assimilation and metabolic fate in plants", Photosynthesis Research, 2005, vol. 86, pp. 373-389.

Sun, G. et al., "Distribution and Translocation of Selenium from Soil to Grain and Its Speciation in Paddy Rice (*Oryza sativa* L.)", Environ. Sci. Technol., 2010, vol. 44, pp. 6706-671.

Williams, P.N. et al., "Selenium Characterization in the Global Rice Supply Chain", Environ. Sci. Technol., 2009, vol. 43, pp. 6024-6030.

Zhu, Y. et al., "Selenium in higher plants: understanding mechanisms for biofortification and phytoremediation", Trends in Plant Science, 2009, vol. 14, No. 8, pp. 436-442.

\* cited by examiner

FIG. 6

SEQUENCE LISTING

<160> NUMBER OF SEQ ID NOS: 11

<210> SEQ ID NO 1
<211> LENGTH: 1803
<212> TYPE: DNA
<213> ORGANISM: Oryza sativa

<400> SEQUENCE: 1

```
atggatctct cgcggccgga atcgtcggac ctgtcgctgg gtttccactc gctcggccac      60
gcccgcgggc acgcggtcac ggggccgctg cggctgttcg atgacatgga ggacgccaag     120
ccggagaaga gcgtcggtgg cggcggagga ggaggggag gaggagggcga ggaggaggat     180 ggggaggaag ggggcgacca gcacttctcc ctcctcggcc acgcgctctg cgtcaagcgt     240
ccacgccgcg cgctctacgg aggcggaggc ggaggcgggg caggaggtgg aggaggagga     300
ggaggggagg cgtcctcctg ctcgtcttcc tcctcgtcgc tgcacccggc gaagcggcag     360
```

```
gcgacggcgg agcgcggcgc ggatctggag gcccgccgcg gcgccgtccg cgcgtggggc    420
aaccaggcgc tggcggaggc cgacccggac gtgcacgcgc tgatggagct cgagcgcgac    480
cgccaggtgc gcgggatcga gctgatcgcg tcggagaact tcgtctgccg cgcggtgctc    540
gaggcgctcg gcagccacct caccaacaag tactctgagg ccatcccgg  ggctcggtac    600
tatgcggga  accagcacat cgacggcatc gagcgcctct gccatgagcg cgccctcgcc    660
gccttcggtc tcgaccccgc ctgctggggg gtcaacgtcc agccatactc ctgcacctct    720
gcaaacctag ctgtttacac aggtctcctc ctgcccaagg accgtatcat ggggctcgag    780
ccgccttccg gtggccatgt cagccacggg tactacacac caagtggtaa gaaggtgtct    840
ggagcatcca tattcttcga gagcttgtcg tacaaggtga atccgcagac tgggtatatt    900
gattacgaca agcttgagga gcgggcaatg gatttccacc ctaagattct catatgtggt    960
gggagctcat accccaggga gtgggatttt gcacggatga ggctcattgc tgataagtgc    1020
ggtgcggtgc tcatgtgcga tatggcacat atcagcgggc ttgttgcggc caaggaatgc    1080
cgtagtccct ttgattactg tgatgtggtt acatcaacta ctcacaagaa tctgagaggt    1140
cctagaggtg gtataatatt tttcaggaga gggaaaaact taaggaggcg tactggatct    1200
tttctcaag  cggatgagaa tgattatgac ttcgaggaca ggataaattt tgcagttttc    1260
ccttcaatgc aaggaggacc ccataataat catattgcag ccttggcgat aactctgaag    1320
caagtagcaa cacctgaata caaagcatac atcatacaag ttaagaaaaa tgcccaagct    1380
ttggcatcag ccttactcag aagaaaatgc agattggtta ctggtggcac cgataaccac    1440
ttggtacttt gggacctcag aaatttaggc ttgactggaa agaactttga gaaggtctgt    1500
gaggcatgcc acatctccat aaataagatg ccgatatatg gggataatgg ctcaatatct    1560
cctgggggtg ttcggattgg aacacctgca atgactacta gaggttgctt ggaagatgac    1620
tttgaggtga tcgcagattt cctcatcaga gccacccaaa tagctagtaa tcttatgaaa    1680
gaacatggaa aaatgcagaa ggaattcctg agaggcctac agaacaataa agatatcata    1740
gaactccgta accaggttga aattttgca  tcgcagtttg caatgccagg ttttgatgta    1800
tga                                                                 1803
```

<210> SEQ ID NO 2
<211> LENGTH: 600
<212> TYPE: PRT
<213> ORGANISM: Oryza sativa

<400> SEQUENCE: 2

Met Asp Leu Ser Arg Pro Glu Ser Ser Asp Leu Ser Leu Gly Phe His
1               5                   10                  15

Ser Leu Gly His Ala Arg Gly His Ala Val Thr Gly Pro Leu Arg Leu
            20                  25                  30

Phe Asp Asp Met Glu Asp Ala Lys Pro Glu Lys Ser Val Gly Gly Gly
        35                  40                  45

Gly Gly Gly Gly Gly Gly Gly Glu Glu Glu Asp Gly Glu Glu Gly
    50                  55                  60

Gly Asp Gln His Phe Ser Leu Leu Gly His Ala Leu Cys Val Lys Arg
65                  70                  75                  80

Pro Arg Arg Ala Leu Tyr Gly Gly Gly Gly Gly Gly Ala Gly Gly
                85                  90                  95

Gly Gly Gly Gly Gly Gly Glu Ala Ser Ser Cys Ser Ser Ser Ser
            100                 105                 110

-continued

```
Ser Leu His Pro Ala Lys Arg Gln Ala Thr Ala Glu Arg Gly Ala Asp
        115                 120                 125
Leu Glu Ala Arg Arg Gly Ala Val Arg Ala Trp Gly Asn Gln Ala Leu
    130                 135                 140
Ala Glu Ala Asp Pro Asp Val His Ala Leu Met Glu Leu Glu Arg Asp
145                 150                 155                 160
Arg Gln Val Arg Gly Ile Glu Leu Ile Ala Ser Glu Asn Phe Val Cys
                165                 170                 175
Arg Ala Val Leu Glu Ala Leu Gly Ser His Leu Thr Asn Lys Tyr Ser
            180                 185                 190
Glu Gly His Pro Gly Ala Arg Tyr Tyr Gly Gly Asn Gln His Ile Asp
        195                 200                 205
Gly Ile Glu Arg Leu Cys His Glu Arg Ala Leu Ala Ala Phe Gly Leu
    210                 215                 220
Asp Pro Ala Cys Trp Gly Val Asn Val Gln Pro Tyr Ser Cys Thr Ser
225                 230                 235                 240
Ala Asn Leu Ala Val Tyr Thr Gly Leu Leu Pro Lys Asp Arg Ile
                245                 250                 255
Met Gly Leu Glu Pro Pro Ser Gly Gly His Val Ser His Gly Tyr Tyr
            260                 265                 270
Thr Pro Ser Gly Lys Lys Val Ser Gly Ala Ser Ile Phe Phe Glu Ser
        275                 280                 285
Leu Ser Tyr Lys Val Asn Pro Gln Thr Gly Tyr Ile Asp Tyr Asp Lys
    290                 295                 300
Leu Glu Glu Arg Ala Met Asp Phe His Pro Lys Ile Leu Ile Cys Gly
305                 310                 315                 320
Gly Ser Ser Tyr Pro Arg Glu Trp Asp Phe Ala Arg Met Arg Leu Ile
                325                 330                 335
Ala Asp Lys Cys Gly Ala Val Leu Met Cys Asp Met Ala His Ile Ser
            340                 345                 350
Gly Leu Val Ala Ala Lys Glu Cys Arg Ser Pro Phe Asp Tyr Cys Asp
        355                 360                 365
Val Val Thr Ser Thr Thr His Lys Asn Leu Arg Gly Pro Arg Gly Gly
    370                 375                 380
Ile Ile Phe Phe Arg Arg Gly Lys Asn Leu Arg Arg Arg Thr Gly Ser
385                 390                 395                 400
Phe Ser Gln Ala Asp Glu Asn Asp Tyr Asp Phe Glu Asp Arg Ile Asn
                405                 410                 415
Phe Ala Val Phe Pro Ser Met Gln Gly Gly Pro His Asn Asn His Ile
            420                 425                 430
Ala Ala Leu Ala Ile Thr Leu Lys Gln Val Ala Thr Pro Glu Tyr Lys
        435                 440                 445
Ala Tyr Ile Ile Gln Val Lys Lys Asn Ala Gln Ala Leu Ala Ser Ala
    450                 455                 460
Leu Leu Arg Arg Lys Cys Arg Leu Val Thr Gly Gly Thr Asp Asn His
465                 470                 475                 480
Leu Val Leu Trp Asp Leu Arg Asn Leu Gly Leu Thr Gly Lys Asn Phe
                485                 490                 495
Glu Lys Val Cys Glu Ala Cys His Ile Ser Ile Asn Lys Met Pro Ile
            500                 505                 510
Tyr Gly Asp Asn Gly Ser Ile Ser Pro Gly Gly Val Arg Ile Gly Thr
        515                 520                 525
Pro Ala Met Thr Thr Arg Gly Cys Leu Glu Asp Asp Phe Glu Val Ile
```

```
                530              535              540
Ala Asp Phe Leu Ile Arg Ala Thr Gln Ile Ala Ser Asn Leu Met Lys
545                 550              555                  560

Glu His Gly Lys Met Gln Lys Glu Phe Leu Arg Gly Leu Gln Asn Asn
                565               570               575

Lys Asp Ile Ile Glu Leu Arg Asn Gln Val Glu Asn Phe Ala Ser Gln
                580              585              590

Phe Ala Met Pro Gly Phe Asp Val
            595             600

<210> SEQ ID NO 3
<211> LENGTH: 1803
<212> TYPE: DNA
<213> ORGANISM: Oryza sativa

<400> SEQUENCE: 3
```

| | | | | | |
|---|---|---|---|---|---|
| atggatctct | cgcggccgga | atcgtcggac | ctgtcgctgg | gtttccactc | gctcggccac | 60 |
| gcccgcgggc | acgcggtcac | ggggccgctg | cggctgttcg | atgacatgga | ggacgccaag | 120 |
| ccggagaaga | gcgtcggtgg | cggcggagga | ggaggggagg | aggaggcga | ggaggaggat | 180 |
| ggggaggaag | gggcgaccca | gcacttctcc | ctcctcggcc | acgcgctctg | cgtcaagcgt | 240 |
| ccacgccgcg | cgctctacgg | aggcggaggc | ggaggcgggg | caggaggtgg | aggaggagga | 300 |
| ggaggggagg | cgtcctcctg | ctcgtcttcc | tcctcgtcgc | tgcacccggc | gaagcggcag | 360 |
| gcgacggcgg | agcgcggcgc | ggatctggag | gcccgccgcg | gcgccgtccg | cgcgtggggc | 420 |
| aaccaggcgc | tggcggaggc | cgaccccgac | gtgcacgcgc | gatggagct | cgagcgcgac | 480 |
| cgccaggtgc | gcgggatcga | gctgatcgcg | tcggagaact | tcgtctgccg | cgcggtgctc | 540 |
| gaggcgctcg | gcagccacct | caccaacaag | tactctgagg | ccatcccgg | ggctcggtac | 600 |
| tatggcggga | accagcacat | cgacggcatc | gagcgcctct | gccatgagcg | cgccctcgcc | 660 |
| gccttcggtc | tcgaccccgc | tgctggggg | gtcaacgtcc | agccatactc | ctgcacctct | 720 |
| gcaaacctag | ctgtttacac | aggtctcctc | ctgcccaagg | accgtatcat | ggggctcgag | 780 |
| ccgccttccg | gtggccatgt | cagccacggg | tactacacac | aagtggtaa | gaaggtgtct | 840 |
| ggagcatcca | tattcttcga | gagcttgtcg | tacaaggtga | atccgcagac | tgggtatatt | 900 |
| gattacgaca | gcttgagga | gcgggcaatg | gatttccacc | ctaagattct | catatgtggt | 960 |
| gggagctcat | accccaggga | gtgggatttt | gcacggatga | ggctcattgc | tgataagtgc | 1020 |
| ggtgcggtgc | tcatgtgcga | tatggcacat | atcagcgggc | ttgttgcggc | caaggaatgc | 1080 |
| cgtagtccct | ttgattactg | tgatgtggtt | acatcaacta | ctcacaagaa | tctgagaggt | 1140 |
| cctagaggtg | gtataatatt | tttcaggaga | gggaaaaact | taaggaggcg | tactggatct | 1200 |
| ttttctcaag | cggatgagaa | tgattatgac | ttcgaggaca | ggataaattt | tgcagttttc | 1260 |
| ccttcaatgc | aaggaggacc | ccataataat | catattgcag | ccttggcgat | aactctgaag | 1320 |
| caagtagcaa | cacctgaata | caaagcatac | atcatacaag | ttaagaaaaa | tgcccaagct | 1380 |
| ttggcatcag | ccttactcag | aagaaaatgc | agattggtta | ctggtggcac | cgataaccac | 1440 |
| ttggtacttt | gggacctcag | aaatttaggc | ttgactggaa | agaactttga | gaaggtctgt | 1500 |
| gaggcatgcc | acatctccat | aaataagatg | ccgatatatg | gggataatgg | ctcaatatct | 1560 |
| cctgggggtg | ttcggattgg | aacacctgca | atgactacta | gaggttgctt | ggaagatgac | 1620 |
| tttgaggtga | tcgcagattt | cctcatcaga | gccacccaaa | tagctagtaa | tcttatgaaa | 1680 |
| gaacatggaa | aaatgcagaa | ggaattcctg | agaggcctac | agaacaataa | agatatcata | 1740 |

```
gaactccgta accaggttga gaattttgca tcgcagtttg caatgccagg ttttgatgta   1800
tga                                                                 1803
```

<210> SEQ ID NO 4
<211> LENGTH: 600
<212> TYPE: PRT
<213> ORGANISM: Oryza sativa

<400> SEQUENCE: 4

```
Met Asp Leu Ser Arg Pro Glu Ser Ser Asp Leu Ser Leu Gly Phe His
1               5                   10                  15

Ser Leu Gly His Ala Arg Gly His Ala Val Thr Gly Pro Leu Arg Leu
            20                  25                  30

Phe Asp Asp Met Glu Asp Ala Lys Pro Glu Lys Ser Val Gly Gly Gly
        35                  40                  45

Gly Gly Gly Gly Gly Gly Gly Glu Glu Glu Asp Gly Glu Glu Gly
    50                  55                  60

Gly Asp Gln His Phe Ser Leu Leu Gly His Ala Leu Cys Val Lys Arg
65                  70                  75                  80

Pro Arg Arg Ala Leu Tyr Gly Gly Gly Gly Gly Ala Gly Gly
                85                  90                  95

Gly Gly Gly Gly Gly Gly Glu Ala Ser Ser Cys Ser Ser Ser Ser
            100                 105                 110

Ser Leu His Pro Ala Lys Arg Gln Ala Thr Ala Glu Arg Gly Ala Asp
        115                 120                 125

Leu Glu Ala Arg Arg Gly Ala Val Arg Ala Trp Gly Asn Gln Ala Leu
130                 135                 140

Ala Glu Ala Asp Pro Asp Val His Ala Pro Met Glu Leu Glu Arg Asp
145                 150                 155                 160

Arg Gln Val Arg Gly Ile Glu Leu Ile Ala Ser Glu Asn Phe Val Cys
                165                 170                 175

Arg Ala Val Leu Glu Ala Leu Gly Ser His Leu Thr Asn Lys Tyr Ser
            180                 185                 190

Glu Gly His Pro Gly Ala Arg Tyr Tyr Gly Gly Asn Gln His Ile Asp
        195                 200                 205

Gly Ile Glu Arg Leu Cys His Glu Arg Ala Leu Ala Ala Phe Gly Leu
    210                 215                 220

Asp Pro Ala Cys Trp Gly Val Asn Val Gln Pro Tyr Ser Cys Thr Ser
225                 230                 235                 240

Ala Asn Leu Ala Val Tyr Thr Gly Leu Leu Pro Lys Asp Arg Ile
                245                 250                 255

Met Gly Leu Glu Pro Pro Ser Gly Gly His Val Ser His Gly Tyr Tyr
            260                 265                 270

Thr Pro Ser Gly Lys Lys Val Ser Gly Ala Ser Ile Phe Phe Glu Ser
        275                 280                 285

Leu Ser Tyr Lys Val Asn Pro Gln Thr Gly Tyr Ile Asp Tyr Asp Lys
    290                 295                 300

Leu Glu Glu Arg Ala Met Asp Phe His Pro Lys Ile Leu Ile Cys Gly
305                 310                 315                 320

Gly Ser Ser Tyr Pro Arg Glu Trp Asp Phe Ala Arg Met Arg Leu Ile
                325                 330                 335

Ala Asp Lys Cys Gly Ala Val Leu Met Cys Asp Met Ala His Ile Ser
            340                 345                 350
```

-continued

Gly Leu Val Ala Ala Lys Glu Cys Arg Ser Pro Phe Asp Tyr Cys Asp
            355                 360                 365

Val Val Thr Ser Thr Thr His Lys Asn Leu Arg Gly Pro Arg Gly Gly
    370                 375                 380

Ile Ile Phe Phe Arg Arg Gly Lys Asn Leu Arg Arg Arg Thr Gly Ser
385                 390                 395                 400

Phe Ser Gln Ala Asp Glu Asn Asp Tyr Asp Phe Glu Asp Arg Ile Asn
                405                 410                 415

Phe Ala Val Phe Pro Ser Met Gln Gly Pro His Asn Asn His Ile
                420                 425                 430

Ala Ala Leu Ala Ile Thr Leu Lys Gln Val Ala Thr Pro Glu Tyr Lys
            435                 440                 445

Ala Tyr Ile Ile Gln Val Lys Lys Asn Ala Gln Ala Leu Ala Ser Ala
        450                 455                 460

Leu Leu Arg Arg Lys Cys Arg Leu Val Thr Gly Gly Thr Asp Asn His
465                 470                 475                 480

Leu Val Leu Trp Asp Leu Arg Asn Leu Gly Leu Thr Gly Lys Asn Phe
                485                 490                 495

Glu Lys Val Cys Glu Ala Cys His Ile Ser Ile Asn Lys Met Pro Ile
                500                 505                 510

Tyr Gly Asp Asn Gly Ser Ile Ser Pro Gly Gly Val Arg Ile Gly Thr
            515                 520                 525

Pro Ala Met Thr Thr Arg Gly Cys Leu Glu Asp Asp Phe Glu Val Ile
        530                 535                 540

Ala Asp Phe Leu Ile Arg Ala Thr Gln Ile Ala Ser Asn Leu Met Lys
545                 550                 555                 560

Glu His Gly Lys Met Gln Lys Glu Phe Leu Arg Gly Leu Gln Asn Asn
                565                 570                 575

Lys Asp Ile Ile Glu Leu Arg Asn Gln Val Glu Asn Phe Ala Ser Gln
            580                 585                 590

Phe Ala Met Pro Gly Phe Asp Val
        595                 600

<210> SEQ ID NO 5
<211> LENGTH: 38
<212> TYPE: DNA
<213> ORGANISM: Artificial Sequence
<220> FEATURE:
<223> OTHER INFORMATION: Synthetic, forward OsSHM4 gene sequence
      complementation primer

<400> SEQUENCE: 5
agaggatccc cgggtacctt gtttgctagg attgggtt                           38

<210> SEQ ID NO 6
<211> LENGTH: 39
<212> TYPE: DNA
<213> ORGANISM: Artificial Sequence
<220> FEATURE:
<223> OTHER INFORMATION: Synthetic, reverse OsSHM4 gene sequence
      complementation primer

<400> SEQUENCE: 6
attgttaatt aagaattcga tgctagacag aggccgagt                          39

<210> SEQ ID NO 7
<211> LENGTH: 24
<212> TYPE: DNA
<213> ORGANISM: Artificial Sequence

```
<220> FEATURE:
<223> OTHER INFORMATION: Synthetic, forward sgRNA knockout target primer

<400> SEQUENCE: 7
ggcaaggctc attgctgata agtg                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic, reverse sgRNA knockout target primer

<400> SEQUENCE: 8
aaaccactta tcagcaatga gcct                                          24

<210> SEQ ID NO 9
<211> LENGTH: 18
<212> TYPE: DNA
<213> ORGANISM: Artificial Sequence
<220> FEATURE:
<223> OTHER INFORMATION: Synthetic, forward primer for hygromycin marker

<400> SEQUENCE: 9
gcccaaggac cgtatcat                                                 18

<210> SEQ ID NO 10
<211> LENGTH: 20
<212> TYPE: DNA
<213> ORGANISM: Artificial Sequence
<220> FEATURE:
<223> OTHER INFORMATION: Synthetic, reverse primer for hygromycin marker

<400> SEQUENCE: 10
gcattgtgat gttgaatggt                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic, knockout target sequence of a first
      exon of the OsSHM4 genes

<400> SEQUENCE: 11
aggctcattg ctgataagtg                                               20
```

RICE SERINE HYDROXYMETHYLTRANSFERASE CODED GENE *OSSHM4* MUTANTS AND APPLICATION THEREOF

CROSS-REFERENCE TO RELATED APPLICATIONS

This application is claiming priority of Chinese Patent Application No. 201910085873.X, filed Jan. 29, 2019, the contents of each of which are hereby incorporated by reference into the application.

BACKGROUND

Reference to a Sequence Listing

This application incorporates-by-reference nucleotide and/or amino acid sequences which are present in the file named "201223_91275_Substitute_Sequence-_Listing_LMO.txt", which is 16.8 kilobytes in size, and which was created Dec. 15, 2020 in the IBM-PC machine format, having an operating system compatibility with MS-Windows, which is contained in the text file tiled Dec. 23, 2020 as part of this application.

Technical Field

The present invention herein belongs to the technical field of plant genetic engineering, and relates to rice serine hydroxymethyltransferase gene OsSHM4 mutants and application thereof.

Related Art

Selenium (Se), an essential element for humans and animals, plays an important role in maintaining a healthy immune system and reducing the risk of cancers (Sors et al., 2005). An average selenium uptake in many regions of China is less than 40 μg $d^{-1}$ recommended. by the World Health Organization (WHO), and even in some selenium-poor regions of China, the selenium uptake is less than 10 μg $d^{-1}$ (Combs, 2001; Chen et al., 2002). In order to reduce the health problems of cancers, cardiovascular diseases, viral diseases and so on caused by selenium deficiency, increasing the selenium content in food is a good way to meet the selenium uptake of humans. Rice is one of the most important staple foods in China, however, the selenium content in rice is often relatively low or even insufficient to meet dietary needs (Williams el al., 2009), so the application of selenium fertilizers can be an effective bioaugmentation method for crops (Hawkesford & Zhao, 2007). Previous studies show that the Se content in rice field soil is within the range of 0.5-47.7 mg $kg^{-1}$, the Se content in rice is linear with the Se content in soil, and the Se concentrations in rice are straw>bran>whole grain>refined rice>rice husk from high to low (Sun et al., 2010). Of course, further studies on a series of processes of absorbing Se by plants from soils, transferring from roots to shoots. and redistributing Se of the shoots will increase Se concentrations in crops more efficiently and economically (Zhu el al., 2009).

Selenate is the main form in alkaline and well-oxidized soil, while selenite is ubiquitous in acidic to neutral soil or in reducing soil such as rice soil (Elramady et al., 2015). Due to the chemical similarity of sulfate and selenate, selenate can be absorbed into roots through sulfate transporters and a mechanism of selenite absorption is not clear. In soil, selenite is readily strongly adsorbed by iron oxides and hydroxides (Barrow & Whelan, 2010), so selenate is a major source of elemental selenium absorption in plants.

At present, reports of genes which directly influence selenium concentration in rice shoots and brown rice are few. The OsSHM4 gene has the accession number AK103554.1 in GenBank and is annotated as Serine hydroxymethyltransferase 4 (SHM4).

SUMMARY

The present invention is directed to provide rice serine hydroxymethyltransferase coded gene OsSHM4 mutants.

The present invention is directed to provide application of the rice serine hydroxymethyltransferase coded gene mutants.

The rice serine hydroxymethyltransferase coded gene OsSHM4 mutants are obtained in a manner that T at a 461st position of a CDS sequence region of a wild type rice OsSHM4 gene is mutated to C, so that coded amino acids thereof are mutated from leucine to proline; a CDS sequence of the wild type rice OsSHM4 gene is shown in SEQ ID NO: 1; and a CDS sequence of the rice serine hydroxymethyltransferase coded gene mutants is shown in SEQ ID NO. 3.

An amino acid sequence of coded proteins of the rice serine hydroxymethyltransferase coded gene mutants is shown in SEQ ID NO. 4.

Further, an expression vector including the rice OsSHM4 gene mutants falls within the scope of protection of the present invention.

Further, a host cell including the rice OsSHM4 gene mutants falls within the scope of protection of the present invention.

The present invention discloses application of the rice serine hydroxymethyltransferase coded gene mutants in enhancing an absorbing capacity of rice roots to sulfate and remarkably improving a total sulfur concentration of rice shoots.

The present invention discloses application of the rice serine hydroxymethyltransferase coded gene mutants in enhancing an absorbing capacity of roots to selenate and remarkably improving a total selenium concentration of rice shoots.

The present invention discloses application of the rice serine hydroxymethyltransferase coded gene mutants in remarkably improving total S and Se concentrations in brown rice without remarkably influencing an agronomic trait.

The present invention discloses application of the coded proteins of the rice serine hydroxymethyltransferase coded gene mutants in enhancing an absorbing capacity of rice roots to sulfate and remarkably improving a total sulfur concentration of rice shoots. The present invention discloses application of the coded proteins of the rice serine hydroxymethyltransferase coded gene mutants in enhancing an absorbing capacity of roots to selenate and remarkably improving a total selenium concentration of rice shoots. The present invention discloses application of the coded proteins of the rice serine hydroxymethyltransferase coded gene mutants in remarkably improving total S and Se concentrations in brown rice without remarkably influencing an agronomic trait.

The present invention has the following beneficial effects:

1, The present invention provides the rice serine hydroxymethyltransferase coded gene OsSHM4 mutants and biological functions thereof for the first time through systematic research.

Figure 1:
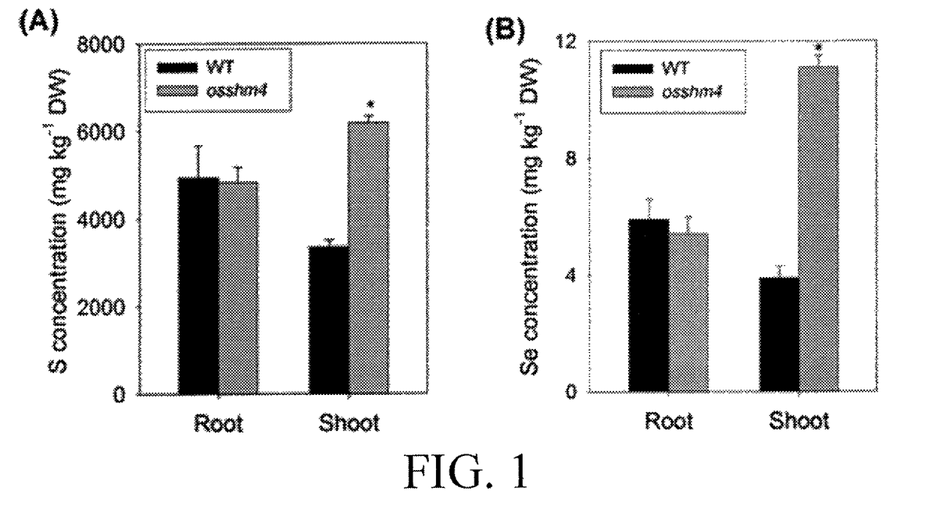
FIG. 1 shows that after OsSHM4 gene mutation, concentrations of sulfur and selenium in shoots are remarkably improved.

2, After serine hydroxymethyltransferase coded genes OsSHM4 are mutated, under a water planting condition, the concentrations of sulfur and selenium in the rice shoots are remarkably improved without influencing the concentrations of sulfur and selenium in the roots (FIG. 1).

Figure 2:
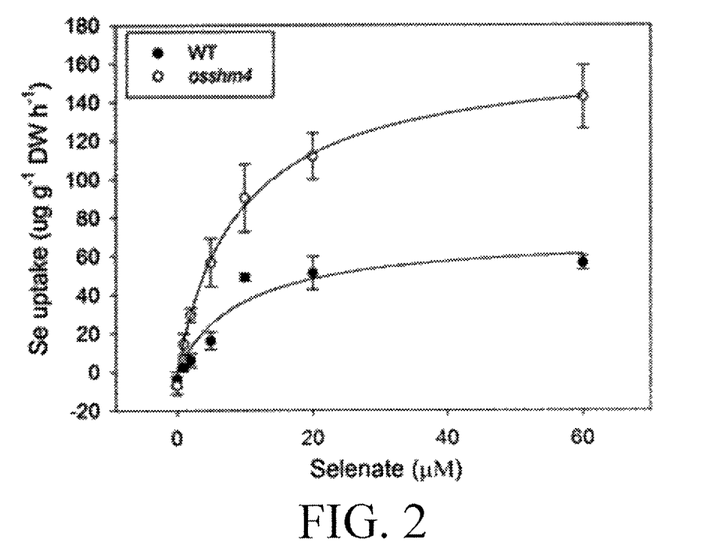
FIG. 2 shows that compared with wide type rice, an absorbing capacity of roots of OsSHM4 gene mutant materials to selenate is remarkably improved.

3, In a selenium absorption kinetics experiment, the Se absorbing capacity of the roots is remarkably improved after the serine hydroxymethyltransferase coded genes OsSHM4 are mutated (FIG 2).

Figure 3:
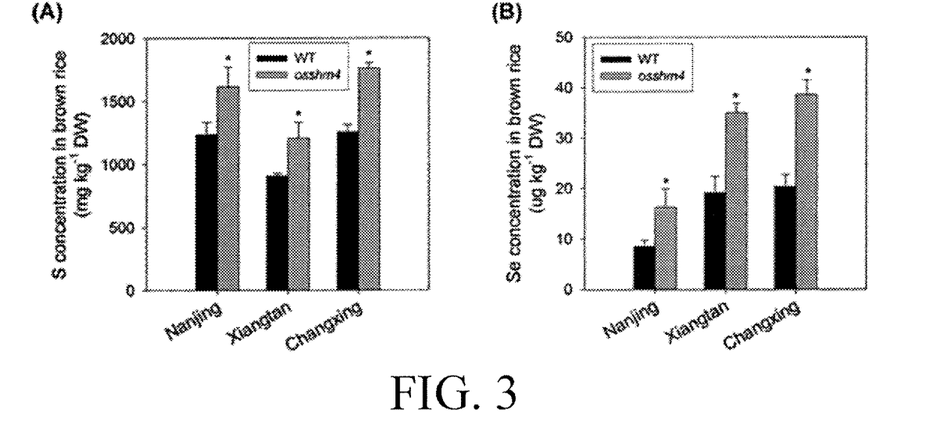
FIG. 3 shows that in a field experiment, compared with wide type rice, more S and Se elements are concentrated in brown rice of OsSHM4 mutant materials.

4, After the serine hydroxymethyltransferase coded genes OsSHM4 are mutated, under a field experiment condition, the sulfur and selenium content of the rice shoots is remarkably improved without influencing the biomass of rice (FIG. 3; Table 1, Table 2).

Figure 4:
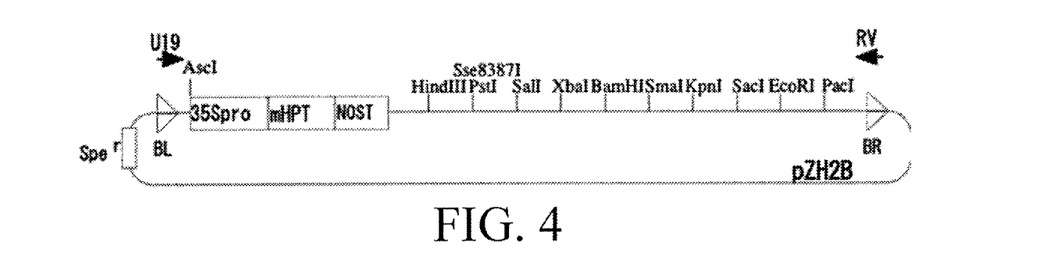
FIG. 4 is a plasmid spectrum of a complementing vector pZH2B.
Figure 5:
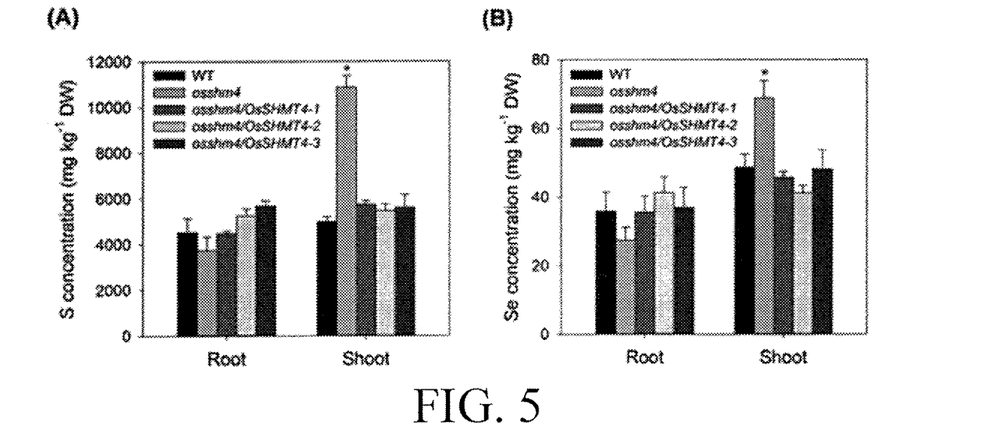
FIG. 5 shows that after wide type OsSHM4 genes complement mutants, total S and Se content of shoots is restored to the level of wide type rice.

5, After the wild type serine hydroxymethyltransferase coded genes OsSHM4 are genetically modified to complement the mutants (FIG. 4), the sulfur and selenium content of the shoots of the complemented strains is restored to that of wild type rice water planting (FIG. 5).

BRIEF DESCRIPTION OF THE DRAWINGS

A: through water planting in a ½ KimuraB nutrient solution for three weeks, total S concentration of the shoots of OsSHM4 mutant materials is more than twice that of wide type rice and total S concentration of roots of the OsSHM4 mutant materials has no difference with that of the wide type rice; and B: through processing with 1 µM of sodium selenate for 72 hours after water planting in a ½ KimuraB nutrient solution for three weeks, total Se concentration of the shoots of the OsSHM4 mutant materials is about three times that of the wide type rice and total Se content of the roots of the OsSHM4 mutant materials has no difference with that of the wide type rice.

A: S concentrations in brown rice of the wide type rice and S concentrations in brown rice of the OsSHM4 mutant materials when planted in different rice fields; and B: Se concentrations in brown rice of the wide type rice and Se concentrations in brown rice of the OsSHM4 mutant materials when planted in different rice fields.

A: through water planting in a ½ KimuraB nutrient solution for three weeks, total sulfur content of shoots of transgenic strains complemented by the wide type OsSHM4 genes is restored to the level of the wide type rice water planting, and complementation succeeds; and B: through processing with 5 µM of sodium selenate for 72 hours after water planting in a ½ KimuraB nutrient solution for three weeks, total selenium content of the shoots of the transgenic strains complemented by the wide type OsSHM4 genes is restored to the level of the wide type rice water planting, and complementation succeeds.

DETAILED DESCRIPTION

The following embodiments are intended to illustrate the present invention and are not intended to limit the scope thereof. Modifications or substitutions to the methods, steps or conditions of the present invention are within the scope of the present invention without departing from the spirit or essence of the present invention.

Embodiment 1 Obtaining of Rice Serine Hydroxymethyltransferase Gene OsSHM4 Mutants 1) A rice ethyl methanesulfonate (EMS) chemical mutagenesis library is constructed, specifically, after about 1 kg of rice seeds (Zhongjiazao 17) are soaked at 37° C. for 24 hours, chemical mutagenesis is carried out with EMS at a final concentration of 1% (V/V) for 8 hours, and then the rice is rinsed with tap water to remove residual EMS. Germination is accelerated for 48 hours under the condition of 37° C. Then the mutagenized rice seeds are sown into a rice field. M2 generations of seeds are harvested from each single plant after the rice is mature, dried and preserved. The construction of a rice mutant library is completed.

2) Screening and gene cloning of rice mutants are carried out, specifically, when a rice mutant library is screened, one cadmium-resistant rice mutant is screened by 2 µM cadmium chloride and subjected to rice whole genome sequencing. A mutant gene is located as a rice serine hydroxymethyltransferase coded gene OsSHM4. A mutation site is mutation of T at a 461st position of a first exon of a CDS sequence region of the OsSHM4 gene to C, and single amino acid substitution (leucine-proline) is caused.

One serine hydroxymethyltransferase coded gene OsSHM4 mutant of Zhongjiazao 17 rice background is obtained in the present embodiment, and other positions of a genome do not mutate except for T-C mutation at the 461st position of the first exon of the CDS sequence region of the rice serine hydroxymethyltransferase coded gene OsSHM4.

Embodiment 2

Comparison on total S concentrations of shoots and roots of osshm4 mutant materials and wide type rice and total Se concentrations of the shoots and the roots of the osshm4 mutant materials and the wide type rice specifically includes the following implementation process.

1) Wild type rice seeds and osshm4 mutant seeds are soaked at 37° C. for 48 hours, rinsed with tap water, sown on a suspended plastic small black mesh, and cultured with a 0.5 mM $CaCl_2$ solution for 1 week, and the solution is changed every three days.

2) Wild type rice seedlings and osshm4 mutant seedlings are transferred to 4 L plastic black barrels for culture and cultured with ½ KimuraB (pH 4.5-5.0) for two weeks. Four wild type rice seedlings and four osshm4 mutant seedlings are planted in the 4 L black barrels respectively, a total of three barrels serve as three biological replicates, and then the seedlings are treated with a sodium selenate nutrient solution with a final concentration of 1 mM for 72 hours.

3) Shoot and root samples are collected, washed three times with deionized water to remove ions and impurities absorbed on the surface, and placed in a 65° C. oven to be dried for 3 days for digestion.

4) All the shoot or root samples are weighed to be put into a graphite digestion tube. 5 mL of mixed acid solution (85%: 15%, V/V, nitric acid: perchloric acid, guaranteed reagent) is added. Then the graphite digestion tube is placed in a graphite digestion furnace for sample digestion, and temperature control conditions are as follows: 60° C. for 1 hour, 90° C. for 1 hour, 120° C. for 1 hour and 150° C. for 1 hour. Then the residual acid solution in the tube is completely drained off under the 190° C. condition. The volume is made up to 25 mL with a 2% nitric acid solution. The solution is mixed well and then transferred to a 50 mL plastic centrifuge tube.

5) The S and Se content in the sample solution is determined by an inductively coupled plasma mass spectrometry (ICP-MS), and the total S and Se content of shoots and roots of the wild type rice and the mutants is calculated according to a sample amount and a dilution factor.

A result of the present embodiment shows that compared with the wide type rice, more total S is concentrated on the shoots of the osshm4 mutant materials instead of the roots (FIG. 1A), and the total Se content of the shoots of the osshm4 mutant materials is also greatly improved without influencing the Se content of the roots (FIG. 1B).

Embodiment 3

Comparison on absorbing capacities of wide type rice and osshm4 mutant materials to selenate specifically includes the following implementation process.

1) Wild type rice seeds and osshm4 mutant seeds are soaked at 37° C. for 48 hours, rinsed with tap water, sown on a suspended plastic small black mesh, and cultured with a 0.5 mM $CaCl_2$ solution for 1 week, and the solution is changed every three days.

2) Wild type rice seedlings and osshm4 mutant seedlings are transferred to 4 L plastic black barrels for culture and cultured with ½ KimuraB (pH 4.5-5.0) for two weeks for standby.

3) During treatment, the wild type rice seedlings and osshm4 mutant seedlings grown for about three weeks are transferred into a 1 L container and treated with 1 L of sodium selenate solution for 20 minutes respectively, and concentrations are 0, 1, 2, 5, 10, 20 and 60 µM respectively. The water temperature is 28° C. and the room temperature is 28° C. Three biological replicates are set for each concentration, and one biological replicate is three strains of wild type rice and three strains of osshm4 mutant materials in the 1 L container.

4) After treatment for 20 minutes, only roots are taken, then washed three times with deionized water to remove adsorbed ions and impurities, and placed in a 65° C. oven to be dried for 3 days for digestion.

5) Root samples are weighed to be put into a graphite digestion tube. 5 mL of mixed acid solution (85%:15%, V/V, nitric acid: perchloric acid, guaranteed reagent) is added. Then the graphite digestion tube is placed in a graphite digestion furnace for sample digestion, and the temperature control conditions are as follows: 60° C. for 1 hour, 90° C. for 1 hour, 120° C. for 1 hour and 150° C. for 1 hour. Then the residual acid solution in the tube is completely drained off under the 190° C. condition. The volume is made up to 25 mL with a 2% nitric acid solution. The solution is mixed well and then transferred to a 50 mL plastic centrifuge tube.

6) The content of Se absorbed by roots of the wild type rice and the content of Se absorbed by roots of the mutants are finally calculated according to a sample amount and a dilution factor after the content of Se in the sample solution is determined by an inductively coupled plasma mass spectrometry (ICP-MS).

The present embodiment shows that compared with the wide type rice, the absorbing capacity of the roots of the osshm4 mutant materials to sodium selenate [Se(V)] is greatly improved (FIG. 2), After linear fitting, the Km value (WT, 9.4±4.6 µM vs osshm4, 9.0±0.8 µM) has no change while the Vmax value (WT, 70.6±12.1 mg $kg^{-1}$ $h^{-1}$ vs cdtl, 164.3±5.6 mg $kg^{-1}$ $h^{-1}$) of the osshm4 mutant materials is remarkably improved, which shows that the Se(V) absorbing capacity of the roots of the osshm4 mutants is remarkably improved.

Embodiment 4

Comparison on total S and Se concentrations in brown rice of wide type rice and osshm4 mutant materials in a field experiment specifically includes the following implementation process.

1) Wild type rice seeds and osshm4 mutant seeds are sown in a seedling raising field for seedling raising. Seedlings are transferred into rice fields when three or four leaves grow up. One plant is arranged in each hole. The interval between every two plants is 10 cm. and the interval between rows is 15 cm. During the period, normal water and nutrient management control and pest control are carried out.

2) The seedlings are planted in rice fields at different sites (Nanjing, Xiangtan and Changxing), and soils are sampled to determine pH values and Se contents.

3) After the rice is mature, brown rice of four single plants is mixed into a sample. Three biological repeats are arranged. The total S and Se content of the brown rice of the wild type rice and the osshm4 mutants is determined.

4) After the rice is mature, ten single rice plants in the middle of each row are selected to determine agronomic traits of the wild type rice and the osshm4 mutants, and the plants are shorn off at contact positions of shoots and soil during sampling.

5) The total S and Se content of brown rice is determined, specifically, 0.25 g of dried brown rice is weighed to be placed into a microwave digestion tube. 5 ml of concentrated nitric acid (guaranteed reagent) is added for microwave digestion. Then the residual acid solution is removed at 160° C., and after acid removal is completed, the volume is made up to 10 mL with 5% nitric acid, and then the solution is transferred to a 15 mL centrifuge tube for storage. The S content in brown rice samples is determined through ICP-MS, and the Se content in the brown rice samples is determined through a liquid chromatography-atomic fluorescence spectrometer (LC-AFS8500).

6) The value of a soil sample is determined, specifically, 10 g of ground dried rice field soil is weighed. 25 mL of deionized water is added. The mixture stands after being mixed evenly, and the pH value of upper-layer liquid is determined by a pH meter after the soil completely settles.

7) The total Se content of soil is determined, specifically, 0.2 g of ground dried rice field soil is weighed to be put into a graphite digestion tube. 4 ml of concentrated hydrochloric acid (guaranteed reagent) is added. Then 1 ml of concentrated nitric acid (guaranteed reagent) is added, and the digestion temperature of the soil sample is controlled as follows:

| Stage | Temperature control (° C.) | Time (minute) |
| --- | --- | --- |
| 1 | 0-35 | 35 |
| 2 | 35 | 180 |
| 3 | 35-60 | 25 |
| 4 | 60 | 180 |
| 5 | 60-105 | 20 |
| 6 | 105 | 60 |
| 7 | 105-125 | 10 |
| 8 | 125 | 120 |

-continued

| Stage | Temperature control (° C.) | Time (minute) |
|---|---|---|
| | Overnight (opening a cover and adding 5 ml of 20% nitric acid through a pipette) | |
| 1 | 0-80 | 40 |
| 2 | 80 | 30 |

8) After digestion is finished, the volume is made up to 25 mL with 2% nitric acid, vortexed and allowed to stand, and supernatant is poured into a 50 mL centrifuge tube for storage. A supernatant solution is taken in a centrifugal mode to be detected, and the determination method is the same as the determination of Se in brown rice.

The result of the present embodiment shows that when the wild type rice and the osshm4 mutants are planted in rice fields at different sites, compared with the wide type rice, more S and more Se are enriched in brown rice of the osshm4 mutants (FIG. 3A) and (FIG. 3B), and an agronomic trait does not change much (Table 1). In general, the pH value of soil in each rice field is meta-acid and the Se content of the soil is low and below 1 mg kg$^{-1}$ (Table 2).

TABLE 1

Agronomic trait indexes of wide type rice and OsSHM4 mutant materials under different planting sites

| Experimental sites | Sample | Plant height(cm) | Effective tiller number(plant$^{-1}$) | Kernels per spike | Maturing rate(100%) | Thousand seed weight(g) | Yield per plant(g) |
|---|---|---|---|---|---|---|---|
| Nanjing | WT | 85.2 ± 3.7a | 10 ± 2a | 149 ± 14a | 78 ± 3a | 20.6 ± 0.7a | 26.0 ± 4.7a |
| | osshm4 | 81.6 ± 4.9a | 10 ± 2a | 126 ± 11b | 67 ± 5b | 19.5 ± 0.5b | 20.8 ± 5.2b |
| Xiangtan | WT | 79.4 ± 1.4a | 16 ± 3a | 101 ± 15a | 68 ± 7a | 20.0 ± 0.8a | 25.3 ± 5.7a |
| | osshm4 | 80.3 ± 2.9a | 16 ± 3a | 111 ± 12a | 69 ± 5a | 19.1 ± 0.5b | 25.9 ± 7.2a |
| Changxing | WT | 82.3 ± 5.0a | 13 ± 2a | 128 ± 30a | 84 ± 9a | 23.2 ± 0.7a | 29.3 ± 3.4a |
| | osshm4 | 78.4 ± 2.5b | 15 ± 3a | 116 ± 23a | 80 ± 8a | 23.9 ± 0.9a | 25.8 ± 7.1a |

TABLE 2 pH value and total Se content office field soil samples under different planting sites

| Experimental site | pH value | Se content of soil (mg kg$^{-1}$ DW) |
|---|---|---|
| Nanjing | 7.66 ± 0.04 | 0.61 ± 0.03 |
| Xiangtan | 4.84 ± 0.09 | 0.93 ± 0.03 |
| Changxing | 6.44 ± 0.03 | 0.40 ± 0.05 |

Embodiment 5

Wide type serine hydroxymethyltransferase coded genes OsSHM4 are complemented to mutants osshm4, whether mutation phenotypes of high S and Se concentrations of shoots are complemented successfully or not is verified, and the specific implementation process is as follows:

An OsSHM4 gene sequence is amplified by a Prime-STAR® GXL DNA Polymerase (Takara) high fidelity enzyme by using a wild type rice genome DNA as a template and a complementation primer sequence as shown below and is inserted between enzyme cutting sites PstI and KpnI of a plant double-source expression vector pZH2B by using a homologous recombination mode (FIG. 4). After the construction is finished, sequencing verification is carried out, and plasmids are stored for later use.

Complementation primers are as follows:

OsSHM4-Com-F:
(SEQ ID NO. 5)
AGAGGATCCCCGGGTACCTTGTTTGCTAGGATTGGGTT

OsSHM4-Com-R:
(SEQ ID NO. 6)
ATTGTTAATTAAGAATTCGATGCTAGACAGAGGCCGAGT

The constructed plasmids are sent to Wuhan BioRun Biological Company to complete the transgenic work of mutant rice, and the rice mutant osshm4 is used as the transgenic background.

The DNA of a single plant leaf of a positive transgenic strain is extracted. The fragments are amplified by using the primers to carry out sequencing verification, and finally a positive transgenic complemented strain is selected, and self breeding is continuously carried out to obtain T3-generation homozygous materials to be used in a subsequent complementing phenotype verification experiment.

Seeds of wild type rice, osshm4 mutants and three independent transgenic complemented strains are soaked at 37° C. for 48 hours, rinsed with tap water, sown on a suspended plastic mesh, and cultured with a 0.5 mM $CaCl_2$ solution for 1 week, and the solution is changed every three days. Then seedlings are transferred to 4 L plastic black barrels to be cultured with ½ Kimura B (pH 4.5-5.0) for two weeks.

Four strains of wide type rice, four strains of osshm4 mutants and four strains of each of three independent transgenic complemented strains are planted in the 4 L plastic black barrels respectively. A total of three barrels serve as three biological replicates, and then the seedlings are treated with a sodium selenite [Se(VI)] nutrient solution with a final concentration of 5 mM for 72 hours.

Shoot and root samples are collected, washed three times with deionized water to remove ions and impurities adsorbed on the surface, and placed in a 65° C. oven to be dried for 3 days for digestion. All the shoot or root samples are weighed to be put into a graphite digestion tube. 5 mL of mixed acid solution (85%:15%, V/V, nitric acid: perchloric acid, guaranteed reagent) is added. Then the graphite digestion tube is placed in a graphite digestion furnace for sample digestion, and the temperature control conditions are as follows: 60° C. for 1 hour, 90° C. for 1 hour, 120° C. for 1 hour and 150° C. for 1 hour. Then the residual acid solution in the tube is completely drained off under the 190° C. condition. The volume is made up to 25 mL with a 2% nitric acid solution. The solution is mixed well and then transferred to a 50 mL plastic centrifuge tube.

After S and Se content in the sample solution is determined by an inductively coupled plasma mass spectrometry (ICP-MS), the total S and Se content of shoots and roots is calculated according to a sample amount and a dilution factor.

A result of the present embodiment (FIG. 5) shows that the total S and Se content of the shoots of the wild type gene OsSHM4 transgenic complemented strains has been restored to the normal level of wild type rice, which demonstrates that the serine hydroxymethyltransferase coded genes OsSHM4 influence the high S and Se concentration phenotypes of the shoots of the rice mutants.

Embodiment 6

A rice OsSHM4 gene point mutation material is constructed and verified through a crisper gene knockout technology, and the specific implementation process is as follows.

1) Knockout targets sgRNAs on OsSHM4 genes are designed according to a rice OsSHM4 genome sequence by using Broad Institute (http://www.broadinstitute.org/rnai/public/analysis-tools/sgma-design), and are compounded by primers:

```
sgRNA-F(5'-3'):
                                       (SEQ ID NO. 7)
GGCAAGGCTCATTGCTGATAAGTG sgRNA-R(5'-3'):
                                       (SEQ ID NO. 8)
AAACCACTTATCAGCAATGAGCCT
```

Figure 6:
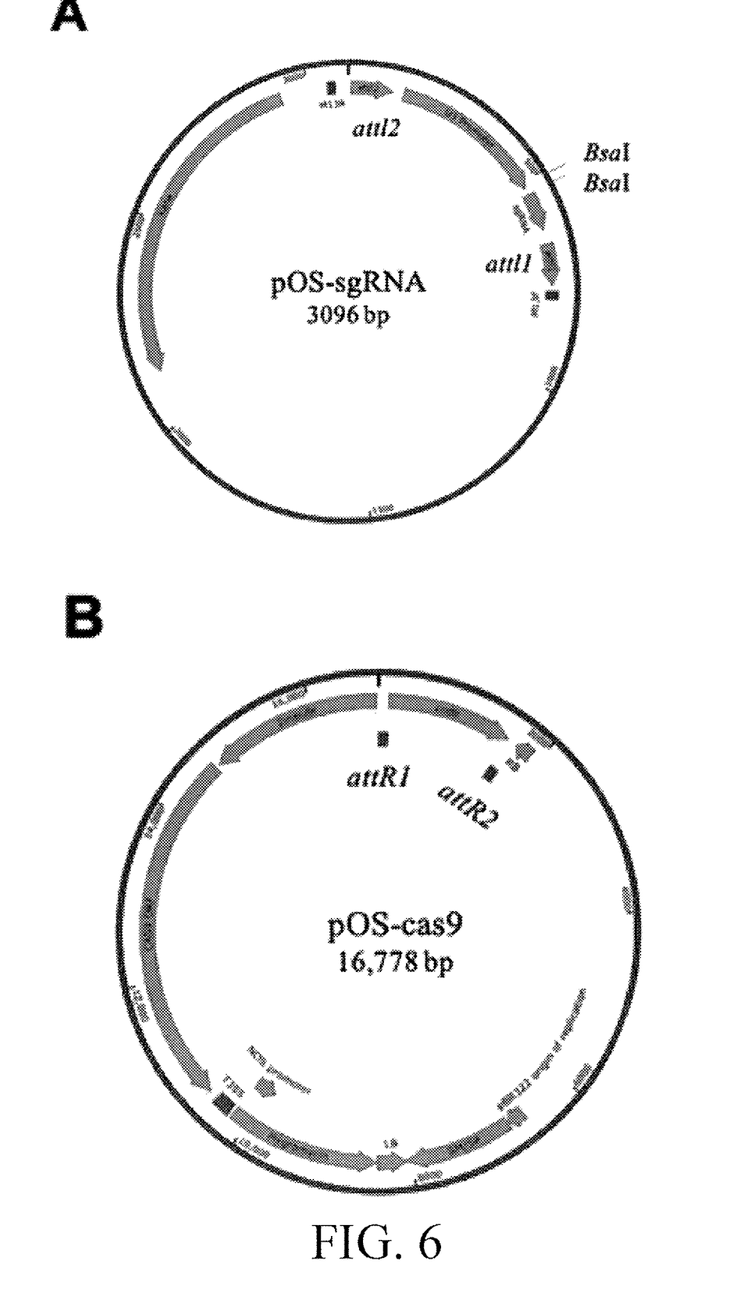
FIG. 6 is a vector pOS-sgRNA spectrum and a vector pOS-cas9 spectrum.

2) The sgRNA-F and sgRNA-R fragments are inserted into a BsaI enzyme cutting site of a linearized vector pOS-sgRNA by T4 ligase. Then an intermediate vector is fused with a final pOS-cas9 by LR reaction in a Gateway method, and a vector spectrum is shown in FIG. 6. After sequencing verification, the genes are sent to Wuhan BioRun Biological Company for rice transgenosis, and the OsSHM4 genes are knocked out by a crispr technology on the background of japonica rice Zhonghua 11 to obtain the point mutation material.

3) A hygromycin marker is configured to screen positive transgenic seedlings. A T0 generation single plant leaf DNA is used as a template. A forward primer is F(5'-3'): GCC-CAAGGACCGTATCAT (SEQ ID NO. 9). A reverse primer is R(5'-3'): GCATTGTGATGTTGAATGGT (SEQ ID NO. 10). A 250 bp sequence upstream and downstream of the knockout targets sgRNA is amplified by PCR. A knockout result of the OsSHM4 genes is verified by sequencing verification, and the knockout targets of crisper knockout are a 999-1019 bp knockout target sequence (5'-AGGCTCAT-TGCTGATAAGTG-3' (SEQ ID NO. 11)) of a first exon of the OsSHM4 genes.

4) The seedlings are strictly related to T2 generations, and homozygous osshm4 knockout mutants are used for phenotype analysis.

5) A result of the present embodiment shows that the total S and Se content of shoots of OsSHM4 point transgenic strains is significantly higher than that of wild type rice, which demonstrates that the loss of functions of the serine hydroxymethyltransferase coded genes OsSHM4 results in high S and Se concentration of the shoots of rice.

REFERENCES

Barrow N J, Whelan B R. 2010. Testing a mechanistic model. VIII. The effects of time and temperature of incubation on the sorption and subsequent desorption of selenite and selenate by a soil. *European Journal of Soil Science* 40: 29-37.

Chen L, Yang F, Xu J, Hu Y, Hu Q, Zhang Y, Pan G. 2002. Determination of selenium concentration of rice in china and effect of fertilization of selenite and selenate on selenium content of rice. *Journal of Agricultural and Food Chemistry* 50: 5128-5130.

Combs G F. 2001. Selenium in global food systems. *British Journal of Nutrition* 85: 517-547.

Elramady H, Abdalla N, Alshaal T, Domokosszabolcsy E Elhawat N, Prokisch J, Sztrik A, Fari M, Elmarsafawy S, Shams M S. 2015. Selenium in soils under climate change, implication for human health. *Environmental Chemistry Letters* 13: 1-19.

Hawkesford M J, Zhao F. 2007. Strategies for increasing the selenium content of wheat. *Journal of Cereal Science* 46: 282-292.

Sors T G, Ellis D R, Salt D E. 2005. Selenium uptake, translocation, assimilation and metabolic fate in plants. *Photosynthesis Research* 86: 373-389.

Sun G, Liu X, Williams P N, Zhu Y. 2010. Distribution and translocation of selenium from soil to grain and its speciation in paddy rice (*Oryza sativa* L.) *Environmental Science & Technology* 44: 6706-6711.

Williams P N, Lombi E, Sun G, Scheckel K G, Zhu Y, Feng X, Zhu J, Carey A, Adomako E E, Lawgali Y. 2009. Selenium characterization in the global rice supply chain. *Environmental Science & Technology* 43: 6024-6030.

Zhu Y-G Pilon-Smits E A H, Zhao F-J, Williams P N, Meharg A A. 2009. Selenium in higher plants: understanding mechanisms for biofortification and phytoremediation. *Trends in Plant Science* 14: 436-442.

What is claimed is:

1. A nucleic acid molecule encoding a rice serine hydroxymethyltransferase mutant having the amino acid sequence set forth as SEQ ID NO: 4.

2. The nucleic acid molecule of claim 1, wherein the rice serine hydroxymethyltransferase mutant has a coding sequence (CDS) set forth as SEQ ID NO: 3.

3. A mutant host rice plant cell comprising the nucleic acid molecule of claim 1.

4. A method for enhancing an absorbing capacity of rice roots to sulfate and improving total sulfur concentration of rice shoots, for enhancing an absorbing capacity of roots to selenate and improving total selenium concentration of rice shoots, or for improving total S and Se concentrations in brown rice without influencing another agronomic trait, the method comprising growing genetically modified rice which contains the nucleic acid molecule of claim 1.

5. The method of claim 4, wherein the serine hydroxymethyltransferase mutant gene contains a CDS sequence set forth as SEQ ID NO: 3.

6. The method of claim 4, wherein the rice is genetically modified by CRISPR technology.

7. The method of claim 4, wherein the biomass of the genetically modified rice is the same as the biomass of a rice that has a genetic background which is identical to the genetically modified rice apart from encoding a wild type serine hydroxymethyltransferase gene.

8. The nucleic acid molecule of claim 1, wherein the molecule is a DNA vector.

9. The DNA vector of claim 8, wherein the vector is an expression vector.

10. A rice plant generated from the host rice plant cell of claim 3.

11. A rice plant comprising a host rice plant cell of claim 3.

12. The host rice plant cell of claim 3, wherein the rice serine hydroxymethyltransferase mutant is encoded by a sequence set forth as SEQ ID NO: 3.

13. A rice plant generated from the host rice plant cell of claim 12.

14. A rice plant comprising a host rice plant cell of claim 12.

* * * * *